United States Patent [19]
Weiss et al.

[11] Patent Number: 5,459,978
[45] Date of Patent: Oct. 24, 1995

[54] STERILIZABLE FLEXIBLE PEEL-SEAL POUCH PACKAGE

[75] Inventors: Mark E. Weiss; Thomas J. Bauer, both of Denver, Colo.; Richard E. Johnson, Appleton, Wis.

[73] Assignees: OnGard Systems Inc, Denver, Colo.; American National Can Company, Chicago, Ill.

[21] Appl. No.: 25,425

[22] Filed: Mar. 1, 1993

[51] Int. Cl.⁶ ............................ B65D 65/40; B65D 81/20; B65B 31/00
[52] U.S. Cl. ........................ 53/425; 206/439; 206/484.1; 383/113
[58] Field of Search .................. 206/438–441, 206/484, 484.1, 484.2; 53/425; 383/113

[56] References Cited

U.S. PATENT DOCUMENTS

| | | |
|---|---|---|
| 3,229,813 | 1/1966 | Crowe, Jr. et al. . |
| 3,410,395 | 11/1968 | Sellers . |
| 3,496,061 | 2/1970 | Freshour et al. . |
| 3,761,013 | 9/1973 | Schuster . |
| 3,768,725 | 10/1973 | Pilaro ................................. 206/439 |
| 3,926,311 | 12/1975 | Laske . |
| 3,930,580 | 1/1976 | Bazell et al. . |
| 3,967,729 | 7/1976 | Tanner, II . |
| 3,991,881 | 12/1976 | Augurt . |
| 4,057,144 | 11/1977 | Schuster ............................ 206/439 |
| 4,168,779 | 9/1979 | Yokokoji et al. . |
| 4,270,658 | 7/1981 | Schuster . |
| 4,367,816 | 1/1983 | Wilkes . |
| 4,407,874 | 10/1983 | Gehrke . |
| 4,514,965 | 5/1985 | Adachi et al. . |
| 4,550,546 | 11/1985 | Raley et al. ....................... 206/439 |
| 4,654,240 | 3/1987 | Johnston . |
| 4,657,804 | 4/1987 | Mays et al. . |
| 4,660,721 | 4/1987 | Mykleby ........................... 206/484.1 |
| 4,724,961 | 2/1988 | Shimoyamada et al. . |
| 4,778,697 | 10/1988 | Genske et al. . |
| 4,857,409 | 8/1989 | Hazelton et al. . |
| 4,937,139 | 6/1990 | Genske et al. . |
| 4,965,109 | 10/1990 | Tucker et al. . |
| 5,071,686 | 12/1991 | Genske et al. . |
| 5,073,436 | 12/1991 | Antonacci et al. . |
| 5,089,308 | 2/1992 | Nordness et al. . |
| 5,093,164 | 3/1992 | Bauer et al. . |
| 5,108,844 | 4/1992 | Blemberg et al. . |
| 5,230,430 | 7/1993 | Kidder .............................. 206/439 |

*Primary Examiner*—Jimmy G. Foster
*Attorney, Agent, or Firm*—Larson and Taylor

[57] ABSTRACT

A steam sterilizable pouch is disclosed. The pouch includes a non-woven steam-permeable bottom web. A multi-layer intermediate web is bonded to the bottom web. The multi-layer web is substantially steam impermeable, except for a perforated steam-permeable region. The intermediate web includes top and bottom layers. A steam-impermeable top web is bonded by a first line heat seal to the top layer of the intermediate web. A cavity having a heat sealable access opening is located between the top web and the top layer. At least a portion of the first line heat seal is peelable after steam sterilization of the pouch at 270° F., the peel strength being from ¾ to 5 pounds per inch. The bonding of the intermediate web to the bottom web is by a second line heat seal that is located peripherally outside of the perforated steam permeable region of the intermediate web.

33 Claims, 3 Drawing Sheets

STERILIZABLE FLEXIBLE PEEL-SEAL POUCH PACKAGE

BACKGROUND OF THE INVENTION

1. Field of the Invention

This invention relates to a sterilizable flexible pouch, to a method of using the pouch, and to apparatus which facilitates use of the pouch. More particularly, the invention relates to pouch packages which are steam sterilizable at high temperatures of up to 270° F. and reliably openable, after such steam sterilization, by way of a reliably openable peel seal. Still more particularly, the invention relates to such packages which are sufficiently large and robust to permit steam sterilization of heavy objects, such as a tray bearing medical devices or instruments.

2. Description of Related Art

Various medical instruments and supplies used in hospitals, are subjected to sterilization treatments such as, for example, steam sterilization, ethylene oxide gas sterilization, radiation sterilization, and dry-heating sterilization, before they are used in medical treatments. Ordinarily, the first step in sterilization is to package or wrap the unsterile device before exposing it to a sterilant. Generally, packages are used for sterilization of small, lightweight objects and wrapping is used for sterilization of heavy objects, particularly metal trays in which one or more objects are held. Such trays are usually made of stainless steel and typically weigh from 5 to 16 pounds, and often up to 30 pounds, when loaded.

In all sterilization treatments, there is a general requirement to observe a sterile technique. In the context of packaging or wrapping, it is particularly important that sterile technique be practiced during unwrapping or during opening of a package. For example, sterile technique does not allow a hand or object to contact a sterile item. It is important, therefore, that any flexible wrapping or packaging material have good drapeability such that it will readily fall away from a sterilized item as the item is unwrapped or as a sterilized package is opened.

A current practice of wrapping a tray for sterilization employs a double-layered muslin cloth, commonly known as CSR wrap, that is secured around an unsterile medical device by taping. Normally, a dust cover is also employed in the post-sterilization phase. CSR wrap, however, is prone to fluid strike-though and exhibits tearing with extended use. In addition, sterilization methods employing cloth wrap are normally practiced by first unwrapping the sterilized tray, followed by moving the unwrapped tray to an area where the tray contents will be used. Sterile technique requires careful and precise procedures. Accordingly, cloth wrap practice is time consuming and expensive.

An alternative practice replaces muslin wrap with a disposable non-woven CSR wrap that is applied in the same manner, i.e., double-layering of wrap secured by taping and use of a dust cover. Although non-woven CSR wraps offer both improved fluid resistance and improved bacterial barrier migration over their cloth counterparts, sterilization practices that use these nonwoven materials are still labor intensive and costly.

Steel or plastic self-contained reusable trays fitted with an outer housing that has a replaceable filter have also been employed as sterilization containers. While the steel tray system offers excellent sterility maintenance, it is not an attractive practice for many hospitals because the containers are extremely expensive. Plastic trays, unlike the steel trays, allow for visual inspection and identification of contents by employing a transparent plastic. Although to a lesser degree than the steel counterpart, the plastic self-contained sterilization trays are also expensive. Moreover, sterilization trays have considerable mass which gives rise to a problem of sterilant condensate which arises with this method of sterilization.

Sterilization pouches and bags comprised of paper and plastic webs have found wide applications in hospitals. Plastic webs afford easy identification of contents through a transparent plastic web. However, as mentioned above, these applications have been limited to sterilization of small or lightweight objects that are easily packaged.

Kraft paper, both coated and uncoated, is used in such packages for both steam and gas sterilization but is not well suited for heavy objects. Moreover, opening a sealed paper package gives rise to the generation of loose paper fibers, which is undesirable in an operating room or other area where dust is desirably kept to a minimum.

Non-woven materials have been substituted for paper in such packages. For example, sheets of spun-bonded polyolefin such as "Tyvek" are widely used in packages for gas sterilization. "Tyvek" offers greater drapeability and reduced fluid strike-through as compared to Kraft paper. However, Tyvek will not withstand high temperature steam autoclaving, and is not employed as an alternative to CSR wrap in steam sterilization.

It is obviously important that a sterilizable package be reliably sealed, and that it remain sealed after sterilization such that its sterilized contents remain sterilized for the required time, generally for at least 30 days in the case of hospital instruments. It is also important, however, that the sealed sterilized package is reliably opened without requiring excessive force and without the risk of generating fiber "dust". Peelable heat seals or "peel seals" between opposed plastic webs have been proposed as being suitable for both of these important properties. For example, Sellers, U.S. Pat. No. 3,410,395, discloses a package which comprises a laminar sheet material folded onto itself or assembled with another separately formed sheet or panel and heat sealed to form a pouch. The laminar sheet material comprises a perforated heat sealable film, preferably polyethylene, which is laminated with and bonded to a paper sheet. Steam can penetrate both the paper layer and the perforated film layer to enter the pouch. The heat seal between the facing panels or sheets is said to be peelable and the package is said to be able to withstand steam sterilization and able to be peeled open by the application of a moderate opposing pulling force.

At the present time, the vast majority of steam sterilization of instruments and the like is carried out in hospitals and medical facilities with saturated steam at a temperature of at least 270° F. for a standard three minute cycle. These conditions are referred to hereinafter as "conventional steam sterilization conditions". The packages disclosed by Sellers are incapable of undergoing sterilization at these conventional steam sterilization conditions.

Figure 7:
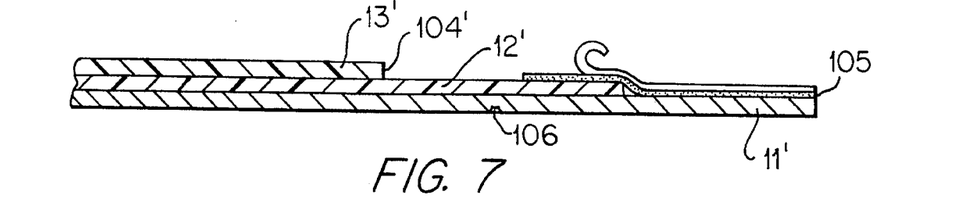
FIG. 7 is an enlarged, diagrammatic cross sectional view along the line 7—7 of FIG. 6.

Wilkes, U.S. Pat. No. 4,367,816 discloses a package which is said to be gas sterilizable, and no mention is made of steam. This package comprises a low density polyethylene sheet which is heat sealed to a laminar tear strip made up of a gas-permeable paper sheet bonded to a perforated plastic film, the latter film being a sheet of high density polyethylene coated on both sides with a thin layer of a blend of ethylene vinyl acetate and low density polyethylene. The latter layer is heat sealed to the low density polyethylene sheet to form a peelable heat seal. Again, however, the materials will fail when the package is subjected to conventional steam sterilization conditions at 270° F. A chevron type package is illustrated in FIG. 7.

SUMMARY OF THE INVENTION

It is an object of the invention to provide a flexible steam-sterilizable pouch package which is steam-sterilizable under coventional steam sterilization conditions at a temperature of at least 270° F. and which is reliably sealed and reliably openable after sterilization by pulling apart a peelable heat seal formed between opposed plastic sheets.

It is a further object to provide such packages which, when sealed, are sufficiently large and robust to permit steam sterilization of heavy objects, such as large trays loaded with medical devices and instruments, and which may be reliably opened by pulling apart a peelable seal without undue force.

It is a further object to provide such packages which, when sealed, are capable of being sterilized under conventional high temperature steam sterilization conditions at a temperature of at least 270° F. and which, after steam sterilization, have a shelf life of at least 30 days.

It is a further object of the invention to provide such packages which permit viewing of the package contents through the packaging material.

It is a further object of the invention to provide such packages which, after sterilization, are openable without tearing of paper or otherwise creating fiber particles.

It is a further object to provide apparatus for facilitating the loading of objects into a sterilization pouch and it is a further object to provide a method of high temperature steam sterilization of a sealed pouch in accordance with the invention.

A steam-sterilizable pouch package according to the invention comprises:

a steam-permeable non-woven bottom web;

a multilayer intermediate web superposed with and bonded to said bottom web, said intermediate web being substantially steam-impermeable, having a perforated region to permit passage of steam, and having a bottom layer and a top layer bonded thereto;

a steam impermeable top web superposed with and bonded to the top layer of said intermediate web by a first line heat seal, said first line heat seal defining limits of a cavity between said top web and said intermediate web for receiving an object to be sterilized, at least one area of said package being free of said first line heat seal, said seal-free area forming an access opening for inserting an item to be sterilized into said cavity, said access opening being sealable such that, when sealed, the sealed access opening forms with said first line heat seal a continuous steam-impervious seal enclosing said cavity, at least a portion of said first line heat seal being a peelable seal which, after steam sterilization of the pouch at a temperature of 270° F., has a peel strength of from ¾ to 5 pounds per inch and is reliably sealed such that the shelf life of a sealed sterilized package is at least 30 days, said peel seal portion of said first line heat seal extending a distance such that, when peeled open, the contents of the cavity are readily removable from said cavity;

said intermediate web being bonded to said bottom web by a second line heat seal peripherally outside the perforated steam-permeable region of said intermediate web such that, when the pouch is sealed, steam can penetrate into said cavity only after passing through said bottom web and then through the perforated region of the intermediate web, said second line heat seal being a permanent fiber tearing heat seal.

A method of sterilizing in accordance with the invention comprises:

(a) providing a pouch which comprises:

a steam-permeable bottom web;

a multilayer intermediate web superposed with and bonded to said bottom web, said intermediate web being substantially steam-impermeable, having a perforated region to permit passage of steam, and having a bottom layer and a top layer bonded thereto;

a steam impermeable top web superposed with and bonded to the top layer of said intermediate web by a first line heat seal, said first line heat seal defining limits of a cavity between said top web and said intermediate web for receiving an object to be sterilized, at least one area of said package being free of said first line heat seal, said seal-free area forming an access opening for inserting an item to be sterilized into said cavity, said access opening being sealable such that, when sealed, the sealed access opening forms with said first line heat seal a continuous steam-impervious seal enclosing said cavity, at least a portion of said first line heat seal being a peelable seal which, after steam sterilization of the pouch at a temperature of 270° F., has a peel strength of from ¾ to 5 pounds per inch and is reliably sealed such that the shelf life of a sealed sterilized package is at least 30 days, said peel seal portion of said first line heat seal extending a distance such that, when peeled open, the contents of the cavity are readily removable from said cavity;

said intermediate web being bonded to said bottom web by a second line heat seal peripherally outside the perforated steam-permeable region of said intermediate web such that, when the pouch is sealed, steam can penetrate into said cavity only after passing through said bottom web and then through the perforated region of the intermediate web said second line heat seal being a permanent fiber tearing heat seal;

(b) placing an object to be sterilized in the cavity of the pouch;

(c) sealing said pouch such that the object to be sterilized is sealed in said cavity and such that steam can penetrate into said cavity only after passing through the bottom web and then through the perforated region of the intermediate web;

(d) and subjecting the sealed pouch to steam sterilization at a temperature of about 270° F. for a time sufficient to sterilize said object.

Apparatus for facilitating the loading of an object into a sealable pouch in accordance with the invention comprises:

(a) an elongate cantilever table member having a substantially flat planar upper surface;

(b) cantilever support means for supporting said table member such that said upper surface is oriented substantially horizontally and such that said table member extends outwardly therefrom such that an open-ended flexible tubular pouch is free to be moved over and envelop said table member such that an object located on the upper surface of the table member is positioned within said tubular pouch; and (c) means for indicating the position of an object on the upper surface of the table member in a position such that a tubular pouch which envelops said table element is free to be moved over said table element to enable an open end of a tubular pouch to be moved beyond an object in said position sufficiently far to enable an open end of the pouch to be sealed.

DESCRIPTION OF PREFERRED EMBODIMENTS

Figure 1:
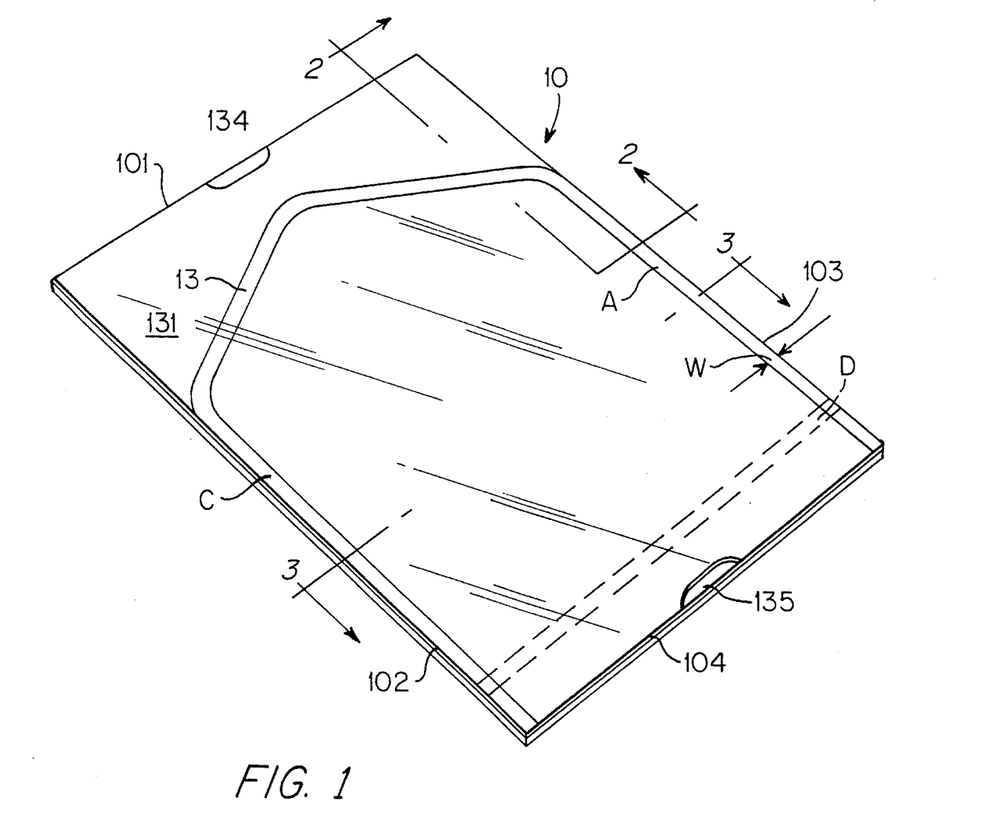
FIG. 1 is a diagrammatic plan view of a first embodiment of a pouch according to the invention.
Figure 2:
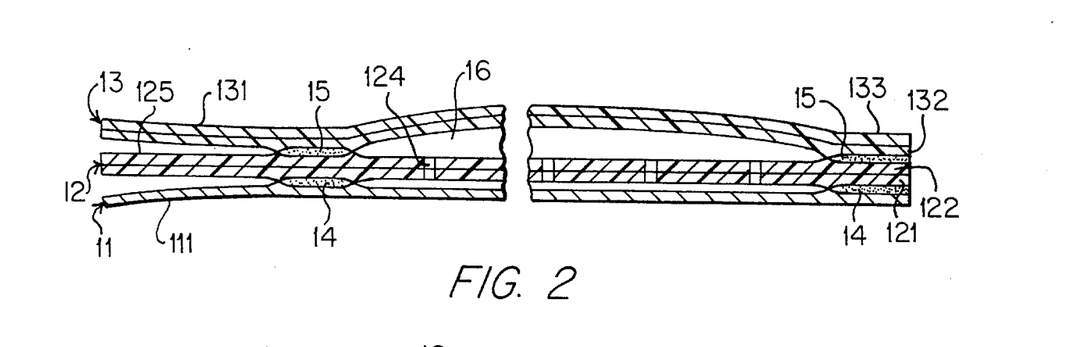
FIG. 2 is a diagrammatic, enlarged, cross sectional view along line 2—2 of FIG. 1.
Figure 3:
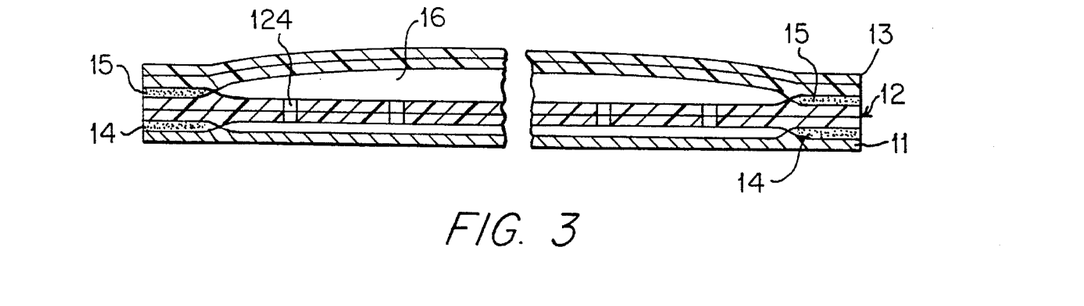
FIG. 3 is a diagrammatic, enlarged, cross sectional view along line 3—3 of FIG. 1.

With reference to FIGS. 1–3, a steam sterilizable pouch 10 in accordance with the invention comprises a steam permeable nonwoven bottom web 11, a plastic intermediate web 12 and a plastic top web 13. While the term "pouch" is used herein, it will be understood that such pouches are also referred to as bags, receptacles, and the like. Bottom web 11 is bonded to intermediate web 12 by a fiber-tearing permanent hermetic heat seal 14. Intermediate web 12 is bonded to top web 13 by a peelable hermetic heat seal 15. Both heat seals are line seals which are provided in regions A, B and C of the webs. The terms "bottom" and "top" are used in the sense in which the pouch is normally oriented in use. It is quite possible to use the pouch with what is referred to herein as the top web lowermost. The top and bottom webs are, however, distinct in that the top web is a steam-impermeable plastic web which is preferably transparent and forms with the plastic intermediate web a cavity for holding an object to be sterilized. The bottom web, on the other hand, is steam-permeable and may be opaque.

Bottom web 11 may be any flexible steam-permeable web which provides an effective barrier against the migration of microorganisms, particularly bacteria, and which is capable of forming a fiber tearing permanent heat seal with the intermediate web, the web and the heat seal both being capable of withstanding steam sterilization at 270° F.

Suitable non-woven material for bottom web 11 includes conventional non-woven materials used in the medical field. Paper and some plastic products, such as spun bonded polyester products are suitable. A preferred material sold under the trademark "Sontara" is a non-woven blend of spunlaced polyester and cellulosic material. Other useful non-woven Sontara products are made up entirely of non-woven polyester or non-woven polyester blended with rayon. Non-woven webs having distinct melt-blown and spun bonded layers such as products having an inner spun bonded layer between outer melt-blown layers are suitable.

One of the principal advantages of the invention is in the ability to use the pouch for steam sterilizing heavy objects weighing up to about thirty pounds. Bottom web 11 together with intermediate web 12 will support the weight of an object in the pouch. If web 12 is sufficiently strong to bear the entire load, the load-bearing strength of web 11 is not of particular concern. Quite the opposite is true, of course, if web 12 has little load bearing strength. The weight of web 11 needed to achieve the desired strength will, of course, depend on the strength-to-weight characteristerics of the web. In view of the foregoing, it will be understood that when considering load-bearing properties only, the weight (i.e., the thickness) of web 11 can vary quite widely. In general it is preferred that webs 11 and 12 together are sufficiently strong to support the full weight of any object for which a particular pouch is designed to accommodate. Since bottom layer 11 is an outer layer, it is preferably abrasion and tear resistant and has the general qualities required for maintenance of sterility.

Web 11 should be sufficiently permeable to steam to permit steam sterilization to be accomplished under conventional conditions at 270° F. for a three minute cycle. Sterilization under these conditions is indicated by a standard test in which test microorganisms are killed to a suitable specified level such as the $10^{-6}$ level. Conventional and widely available web materials of the type mentioned above have more than adequate porosity.

Bottom web 11 must also constitute an adequate barrier against the migration of bacteria. Adequacy in this respect is measured by measuring shelf-life of a sterilized package. Adequate barrier properties are indicated when a sealed package stored at room temperature under ambient conditions, remains sterile after at least 30 days. It will be understood that this property may also be involved in determining the required weight of web 11. Thus, where strength considerations may allow a very light weight web, microbical barrier properties may require a heavier weight. Conventional and widely available webs of the materials mentioned above are readily available in weights which give clearly adequate strength and microbial barrier properties.

Microbial barrier properties may be enhanced by incorporating one or more anti-microbial agents such as a bactericide into the web. For example, the web may be impregnated with a solution of a quaternary ammonium bactericide and then dried to incorporate the bactericide in the web. Similarly, the web may be treated to enhance its water repellancy. For example, the web may be treated with a conventional polysiloxane water repellant.

Intermediate web 12 is a flexible heat sealable plastic web having a bottom layer 121 and a top layer 122. The terms "top" and "bottom" are again used in a sense of the normal orientation of the pouch in use, that is, with the pouch disposed generally horizontally with top web 13 uppermost. Top web 13 is superposed directly above top layer 122 of web 12 and bottom web 11 is positioned directly below bottom layer 121 of web 12. Top and bottom layers 122 and 121 of web 12 are fabricated of heat sealable flexible plastic and are bonded together at least at marginal regions of the layers areas and are preferably coextensive and bonded together across their entire mutually adjacent surfaces. Bonding can be effected by an adhesive seal, by a heat seal, by coextrusion, by lamination of discrete films, or may be effected by means of one or more tie layers interposed between top and bottom layers 121 and 122. Such tie layers may be bonded to the top and bottom layers in any of the ways just mentioned. In a preferred embodiment illustrated in FIG. 4, intermediate web 12 comprises a coextruded web having a bottom layer 121 which is heat sealable with bottom web 11, a top layer 122 which is heat sealable with top web 13, and a tie layer 123 bonding the top and bottom layers.

Middle web 12 is preferably a film as described in copending application Ser. No. 08/025,356 filed Mar. 1, 1993 by Richard E. Johnson and entitled "Sterilizable Packaging Film", now U.S. Pat. No. 4,358,791 issued Oct. 25, 1992 filed Mar. 1, 1994 the disclosure of which is hereby incorporated by reference. Heat seal layer 121 of web 12 is preferably polypropylene or a polypropylene copolymer such as a propylene-ethylene copolymer or blends thereof. Preferred propylene-ethylene copolymers contain ethylene in the range of up to 6%, preferably 1–5%. Heat seal layer 122 of web 12 is preferably polyisobutylene (PIB) modified high density polyethylene (HDPE) in which the PIB content is preferably in a range of about 5 to 60%, more preferably 20 to 40%, and most preferably about 25–35%, or a blend thereof with up to 90% polypropylene and/or one or more propylene copolymers such as those suitable in layer 121. A preferred blend has up to 60% of the polypropylene or propylene copolymer component. A more preferred blend has 40 to 60% PIB modified HDPE and 60–40% of the polypropylene or propylene copolymer component.

Tie layer 123 of web 12 is preferably PIB-modified HDPE as described above. HDPE alone is suitable but is brittle and difficult to co-extrude. Alternatively, the core layer may be a rubber-modified polypropylene and/or one or more copolymers of propylene such as those mentioned above.

Figure 4:
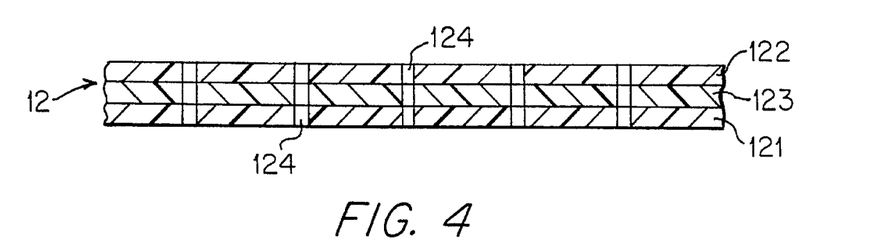
FIG. 4 is a diagrammatic cross sectional view of an alternative form of intermediate web of a pouch according to the invention.

The plastic material of web 12 is essentially impervious to steam and must be perforated as at 124 in FIGS. 2–4 to permit steam to pass through the web. The size and number of perforations 124 may vary widely, the only requirement being to ensure adequate passage of steam for sterilization. Adequacy of permeability is determined as mentioned above in connection with bottom web 11. It is preferred to provide small perforations over the surface of the intermedate web 12. Pinhole size perforations of about 0.05 mm to 1 mm in diameter spaced apart about 0.5 to 5 mm are preferred. Much larger perforations may be employed. Small perforations will not affect the integrity of the heat seals and may extend into the heat seal regions of web 12. Large perforations, however, should be confined to regions peripherally inside the heat seals for seal integrity.

The weight or thickness of intermediate web 12 can vary widely, and considerations similar to those mentioned above are applicable to web 12 although the abrasion and tear resistance are not as important as in an outer web. Preferably, the total thickness of intermediate web 12 will suitably be from 2 to 10 mils, with each of the layers making up the web suitably being from ½ to 5 mils.

Bottom layer 121 is heat sealed at line seal 14 to bottom web 11 at a location peripherally outside of the perforated region of web 12. In the embodiment illustrated in FIGS. 1–3, line heat seal 14 is located at marginal regions A, B, and C adjacent to three sides of the pouch package.

Due to considerations of sterile technique, it is preferred that marginal regions A and C extend along outside edges 102 and 103 of the pouch. However, it is not necessary that the heat seal be at the outside edge of the pouch and the terms "margin", "marginal area" and "marginal region" and the like as used herein are intended to include regions both at the edge of a web as well as to regions which are near to such an edge.

In a preferred embodiment as illustrated in FIG. 1, portion B of the heat seal is spaced peripherally inside end 101 of the pouch in order to provide flange areas 111, 125 and 131, respectively, in webs 11, 12, and 13, the flange areas being peripherally outside of the seal area. The flange portions are used in opening a sealed pouch as described below. Other portions of the heat seal, such as regions A and C which extend along sides 102 and 103 of the pouch indicated in FIG. 1, are preferably provided at or very close to the edges of the pouch in order to minimize the amount of web material required for a given pouch.

Heat seal 14 is a fiber tearing permanent heat seal designed to be retained intact during normal use of the pouch. The strength of permanent heat seal 14 is greater than the tear strength of the weaker of the two webs which it seals and is, of course, very much stronger than peelable seal 15.

In a preferred embodiment, the perforated region of web 12 extends over at least a major portion of the surface area of the web and is more preferably substantially coextensive with the surface area of web 12 which forms a wall of cavity 16. However, the perforated region of web 12 may be considerably smaller, the major consideration being adequate porosity to steam during sterilization. Since the perforated region of web 12 need not be coextensive with web 13, it will be readily apparent that it is necessary only that web 11 be sized to cover the perforated region of web 12, with heat seal 14 being located peripherally outside of the perforated region. A structure of that type will reduce the amount of material needed for web 11, but will complicate the method of making the pouch.

Top layer 122 of web 12 is heat sealed at line seal 15 to top web 13 at a location peripherially outside of cavity 16 of the pouch. In a preferred embodiment, heat seal 15 is provided in the same regions A, B and C as heat seal 14 and is therefore superposed directly over and is both substantially coextensive with and in substantial registration with heat seal 14. Heat seal 15 is a peelable seal, that is, a heat seal which, when pulled open, reliably peels apart without tearing the webs, i.e., webs 11 and 12, which are sealed and without tearing or delaminating either of the two plastic layers, e.g., layers 122 and 132, which together form the peel seal.

Top web 13 is a flexible, steam impermeable plastic web which is heat sealable to top layer 122 of intermediate web 12 and is preferably transparent to permit viewing of objects located in cavity 16. Top web 13 has a heat sealable bottom layer 132 bonded to top layer 133. The terms "top" and "bottom" are again used in the sense of normal use of the package with layer 133 uppermost and with bottom layer 132 superposed directly above cavity 16 and layer 122 of web 12. As in the case of web 12, bonding between layers 132 and 133 is preferably effected across the entire web as in a lamination or a coextrusion. In a preferred embodiment, web 13 is a lamination. However, bonding of the layers can be effected by the use of one or more tie layers, and such bonding need not be effected over the entire surface area of the layers.

The main requirements of web 13 are that it is capable of forming with layer 122 of web 12 a peel seal which is a reliable seal, which is reliably opened by peeling and without tearing as described above, which has a peel strength of from ¾ to 5 pounds per inch and, most importantly, which retains these properties after conventional high temperature steam sterilization for a three minute cycle at a temperature of 270° F. Preferably, peel strength does not vary along its length more than 50%, and more preferably does not vary more than 30%. Peel strength (ASTM test F88) is measured by the force in pounds required to pull apart a peel seal, with the pull being directed along the length of an elongate seal.

Suitable plastic films for top web 13 are disclosed in application Serial No. 08/025,356 (U.S. Pat. No. 4,358,791) mentioned above. Layer 132 of top web 13 is preferably polypropylene and layer 133 of top web 13 is preferably a polyester such as polyethylene terephthalate or nylon, such as cast nylon or biaxially oriented nylon.

The seal width of a pouch in accordance with the invention may vary considerably, but is preferably from ⅛" to 1", more preferably from ⅛" to ¾", and optimally from 5/32" to ½". The width of the peel seal may be, but need not be, substantially the same throughout. For example, it may be desirable to have a wider or narrower peel seal in chevron region B than in regions A and C.

After sterilization, the package is preferably opened manually by grasping with one hand flange area 131 of top web 13 and grasping flange areas 111 and 125 of webs 11 and 12 simultaneously with the other hand and then pulling apart. Drapeability, which imbues a web with the ability to fall away as it is peeled away, is an important attribute, and it is a significant attribute and advantage that the webs of the present invention have a high degree of drapeability. Grasping the flanges is facilitated by providing a cut out area 134 in top web 13 or by providing a siliar cut out in webs 11 and 12. For a rectangular type of pouch as shown in FIG. 1, it is preferred to provide region B as a conventional chevron at one of the narrow ends of the pouch, the angle at the apex of the chevron preferably being from 90° to 150°, and more preferably from 110° to 140°.

The peel seal preferably extends along substantially the full length of heat seal 15. However, it is only required that the peel seal extend a distance along heat seal such that when the peel seal portion of the heat seal is fully peeled open, the contents of cavity 16 are readily accessible. Moreover, it is often desirable to make seal 15 a permanent seal at the end of the seal which is adjacent to the access opening of the pouch. A permanent seal at this point will prevent undesirable premature separation of webs 12 and 13 when an object is inserted into the pouch.

Heat seal 15 defines outer limits of cavity 16 for holding one or more items to be sterilized. Heat seal 15 does not, however, extend completely around cavity 16 as it is necessary to provide the pouch with an access opening to permit insertion into cavity 16 of an object to be sterilized. Heat seal 15 is therefore omitted from at least one marginal region of the pouch to provides access, between webs 12 and 13, into cavity 16. Preferably, a single access opening in seal 15 is provided. In the case of a rectilinear package such as shown in FIG. 1, the access opening is preferably provided at an end 104 of the pouch remote from end 101 which is first employed in opening the sealed pouch. In the preferred embodiment shown, the access opening extends fully across end 104 between seal regions A and C. However, the access opening can extended for a lesser distance and it is not required that the peelable heat seals extend fully to end 104 in regions A and C. In order to minimize inadvertent opening of seal 15 at open end 104 of the pouch, heat seal 15 in the area of regions A and C which are immediately adjacent to open end 104 of the pouch may be made stronger then in the remaining area of regions A and C by suitable control of heat sealing conditions. For example, the heat seal in those areas can be made permanent.

In a preferred embodiment, heat seal 14 is also omitted in the region where the access opening is provided. Thus, in the pouch illustrated in FIGS. 1–3, heat seal 14 is provided directly below heat seal 15 in regions A, B and C, but seals 14 and 15 are both omitted from end 104 of the pouch.

The pouch is preferably rectilinear in plan view and is more preferably rectangular as illustrated. However, it will be readily understood that its shape can be square, oval, round, and of virtually any desired shape.

The pouch has particular utility in steam sterilization, in a hospital or other facility, of trays loaded with one or more re-useable metal instruments and the like. The trays as well as the instruments are usually metal and are quite heavy. The trays are typically made of stainless steel, are rectangular, having a length of 7 to 21 inches, a width of 3 to 13 inches, a height of 2 to 4 inches, and a weight, when loaded, of from 5 to 16 or even up to 30 pounds. For use with such trays, a pouch in accordance with the present invention has a length of about 20 to 36 inches, and a width of 10 to 20 inches. Such trays are commonly sterilized at the current time only after a careful and time-consuming wrapping procedure and it is also necessary to carry out a careful unwrapping procedure before the sterilized instruments can be used. As mentioned above, sterile technique must be maintained. Trays wrapped and unwrapped in this manner can be successfully sterilized under conventional high temperature autoclave conditions at 270° F., but the procedure is time-consuming and exacting. The present pouch avoids the conventional wrapping and unwrapping procedure in that one simply inserts loaded trays into cavity 16, seals the pouch, and inserts the sealed pouch in a conventional high temperature autoclave for sterilization with saturated steam at 270° for the prescribed time which is generally at least a three minute cycle. The sterilized pouch package is then stored until ready for use. Shelf life of a sterilized pouch package is comparable to that of the conventional wrapped trays, and is at least about 30 days. When ready for use, the sterilized pouch package is simply opened manually by grasping the flange areas to open peel seal 15 as described above. The two webs which surround cavity 16 have smooth plastic surfaces which, together with the reliable peeling open of peel seal 15, virtually eliminate the generation of fiber fragments or dust. Thus the present invention provides an alternative to the conventional CSR wrap method of steam sterilization of large heavy objects.

After an object to be sterilized has been inserted into cavity 16, the package is sealed. It is, of course, required to seal the opening, if present, between webs 11 and 12 as well as the access opening between webs 12 and 13. This can be accomplished in any of several ways, such as by providing the package with an adhesive coating or tape or by heat sealing. The pouch illustrated in FIG. 1, for example, is readily heat sealed in marginal region D. Heat sealing can be readily effected by the user by employing conventional and simple heat sealing equipment. Sealing in that event would preferably be conducted to simultaneously provide heat seals 14 and 15 in region D, both of which would be permanent fiber-tearing seals.

Figure 5:
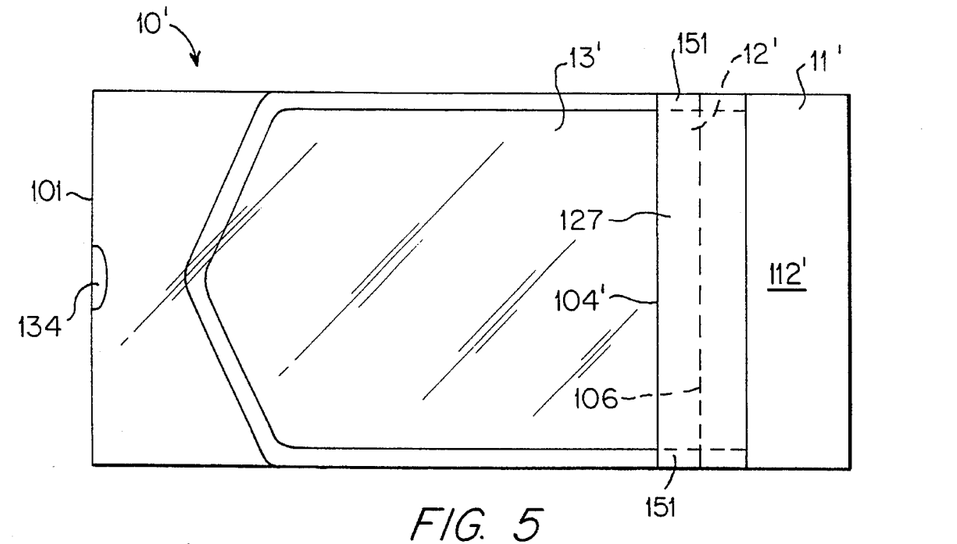
FIG. 5 is a diagrammatic plan view of a second embodiment of a pouch according to the invention.
Figure 6:
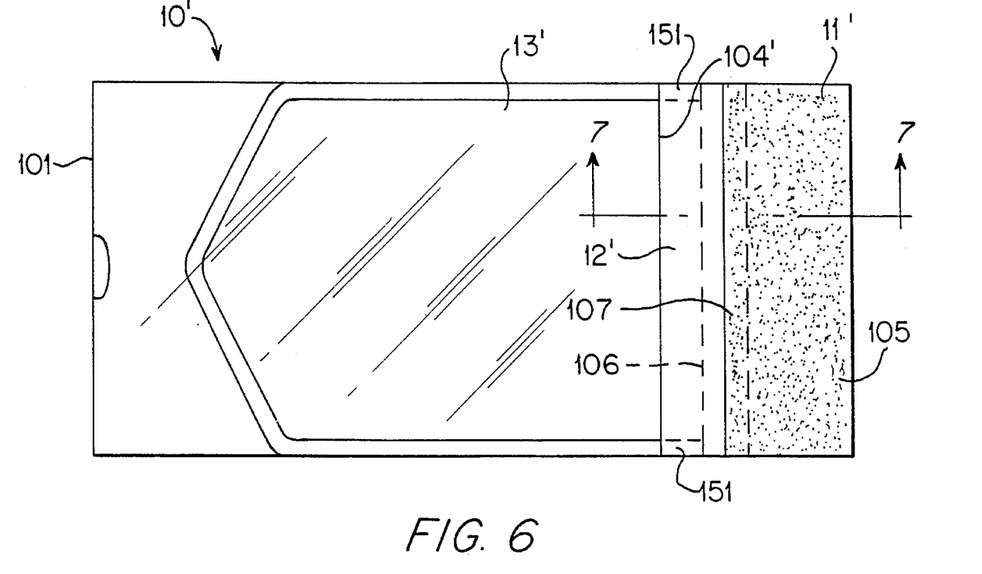
FIG. 6 is a diagrammatic plan view of the pouch of FIG. 5 with an adhesive strip attached thereto.

In a preferred embodiment, the pouch is sealed by an adhesive strip provided on the pouch as illustrated in pouch 10' in FIGS. 5–8. Pouch 10' is the same as pouch 10 of FIGS. 1–3 except that in FIGS. 1–3, webs 11, 12 and 13 are of the same length whereas in FIGS. 5–8, webs 11', 12' and 13' are of progressively decreasing length. At end 101 of the pouch, the ends of webs 11', 12' and 13' are in registration. At the opposite end of the pouch, intermediate web 12' extends outwardly beyond the end of top web 13' forming a first flap region 127 in web 12', and bottom web 11' extends outwardly beyond the end of intermediate web 12' forming a second flap portion 112' in web 11'. With the webs in registration as shown in FIGS. 5 and 6, a length of double sided adhesive tape 105 is applied across the full width of the pouch in position to seal the outer edge of flap portion 127 of intermediate web 12 to the upper surface of flap portion 112' of bottom web 11'. In this embodiment permanent heat seal 14 in areas A and C extends in regions 151 beyond the outer end of top web 11' to the outer end of intermediate web 12'.

Adhesive stock for adhesive strip 105 is widely available and preferably includes a removable release strip 108. The adhesive strip preferably covers substantially all of flap portion 112' of bottom web 11' and about 30 to 60% of flap portion 127 of intermediate web 12'. A fold line 106 is preferably provided across flap 127 at a point located between edge 104' of top web 11' and the inner edge 107 of adhesive strip 105. To seal the access opening of cavity 16 between the top and intermediate webs, the pouch is folded at fold line 106 to bring the outer end of the adhesive strip and bottom web 13' up over the upper surface of top web 13' into the position shown in FIG. 8. The adhesive strip is pressed downwardly and adhered to the upper surfaces of the top and intermediate webs thus sealing the access opening of cavity 16. It is preferred to seal the pouch in the manner depicted in FIGS. 5–8 and in that event the adhesive strip is preferably provided on the pouch as shown in FIGS. 5–7 during the manufacturing process. However, it will be understood that there are several ways in which the pouch may be sealed.

As mentioned above, the invention has particular utility in the steam sterilization of objects carried in trays weighing, when loaded, up to 30 pounds or more. Such trays are fabricated of stainless steel, typically 10"×20"×3", with the bottom of the tray being a screen positioned about ½–¾ inches above the bottom of the tray sides to maintain the tray bottom, i.e., the screen, above a horizontal surface on which the tray is placed.

Figure 9:
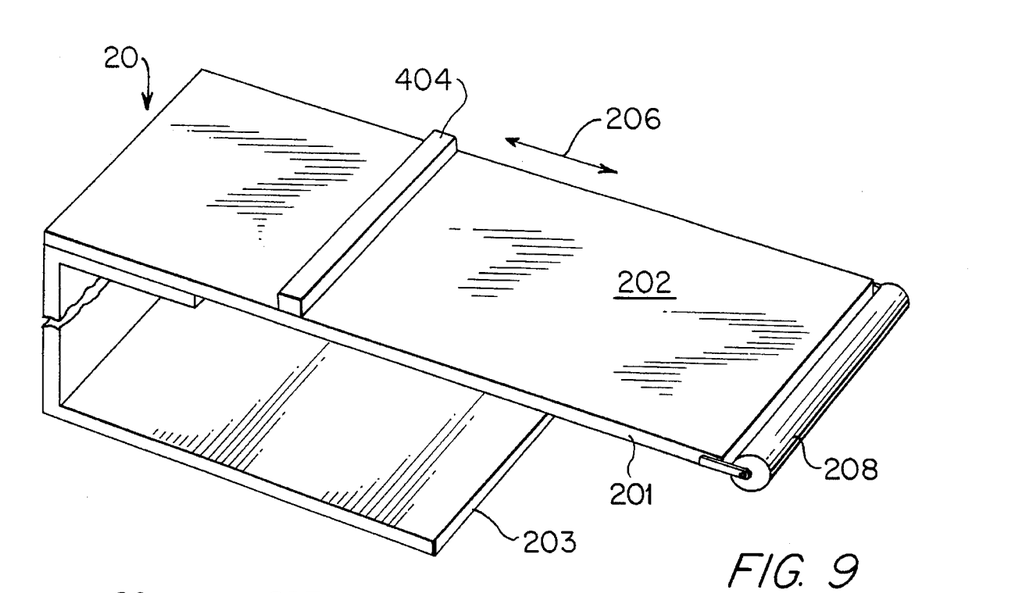
FIG. 9 is a diagrammatic perspective view of apparatus for facilitating the insertion of an object to be sterilized into a pouch according to the invention.
Figure 10:
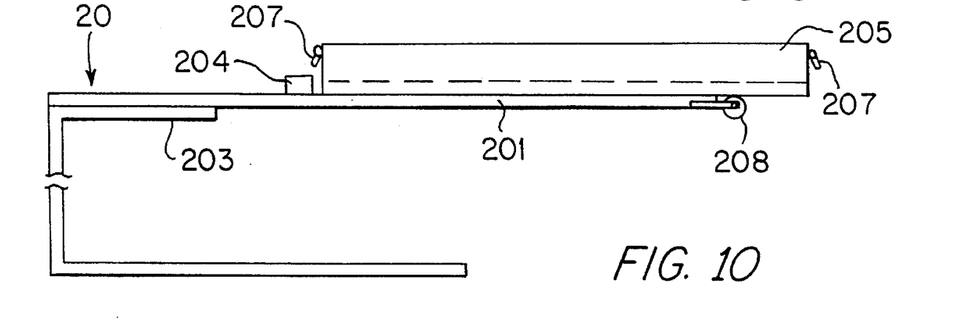
FIG. 10 is a diagrammatic side elevation view of the apparatus of FIG. 7.

Apparatus for facilitating the loading of a tray into a pouch in accordance with the invention is illustrated in FIGS. 9 and 10. Tray loading apparatus 20 includes an elongate cantilever table element 201 having a substantially flat planar upper surface 202 which is intended to be oriented such that surface 202 is oriented substantially horizontally for supporting an item, such as a loaded tray, to be inserted into a sterilization pouch. The apparatus also includes a cantilever support, such as U-shaped support member 203 for supporting table 201 in horizontal position. Support member 203 may include a clamp or the like (not shown) for securing the apparatus to the surface of a table or the like or for otherwise securely mounting the apparatus in fixed position. Surface 202 is preferably wider than the width of a tray to be inserted into the pouch. Table 201 includes an indicator 204 for indicating the position of a tray on surface 202 of the table. Indicator 204 is preferably a stop positioned to be abutted by the end of a tray 205 placed on the table. Stop 204 is preferably releasably secured to table 201 such that its position along the length of table 201 is adjustable in the direction of arrow 206 in order to accommodate trays of different size. In use, tray 205, bearing one or more items to be sterilized, is placed on surface 202 of table 201 with one of its ends abutting stop 204. Conventional trays of this type normally are provided with a handle 207 at each end to facilitate handling.

A sterilizable pouch of proper size for the object to be sterilized is then positioned to the right of loading device 20 with its access opening facing to the left, direction being in the sense of FIGS. 9 and 10. The top and intermediate webs forming the access opening to cavity 16 are separated, and the tubular pouch with its closed end to the right and with its open end to the left is moved to the left such that it is moved over and envelops table 201 and tray 205, thus positioning tray 205 in cavity 16 of the pouch, direction again being in the sense of FIGS. 9 and 10. Stop 204 is positioned on table 201 such that the tubular pouch is free to move (to the left is sense of FIGS. 9 and 10) sufficiently far beyond the object to be sterilized to enable the open end of the tubular pouch to be sealed such that the object to be sterilized is reliably sealed within cavity 16. It will be apparent that indicator 204 need not be a stop and that various indicators may be employed. For example, table 201 could be provided with indicator marks for showing the proper positioning of trays of different size.

The pouch and tray are then removed together from table 201 to enable the pouch to be sealed. Since the pouch is flexible, removal can be effected manually by grasping the object despite the overlying pouch. For example, handles at the end of a tray can be easily grasped in this manner. After being removed from table 201, the pouch and tray are placed on a substantially horizontal surface and the pouch is then sealed as described above. The sealed pouch is then ready for steam sterilization.

Table 201 may be provided with a roller 208 mounted at its distal end to facilitate placement and removal of a heavy tray on the table. For this purpose, roller 208 is mounted such that its uppermost roller surface extends slightly above, in the sense of FIGS. 9 and 10, the plane of surface 202.

Sterilization is effected in conventional high temperature steam sterilizing equipment at a temperature of at least 270° F. and at for at least a three minute cycle. Sterilizable pouches in accordance with the present invention withstand such sterilization conditions without visual effect and without impairment of the integrity of the heat seals or of peelability of the peel seal. Preferably, pouches in accordance with the invention withstand sterilization at 270° F. for at least a 10 minute cycle.

After sterilization, the pouch and object are removed from the autoclave and stored at ambient conditions to await use. Because the pouch webs are flexible, moving a pouch loaded with a heavy tray in and out of an autoclave is facilitated because the tray itself can be grasped when the tray is completely sealed within the pouch. Shelf life of the sterilized pouch is comparable to that of a conventional wrapped tray and is at least 30 days.

Pouches in accordance with the invention are preferably made on pouch-forming machines which are of conventional design and which may be fully automated. It is preferred to form the heat seals simultaneously in a single heating step. However, the heat seals may be made in a series of steps. It is also preferred that the two seals are superposed directly over one another as shown in FIGS. 1–3. In that event, it is preferred to use two opposed heated platens to effect the heat seal, one heated platen bearing against web 11 and the other heated platen bearing against web 13. It will be readily apparent, however, that the seals may be formed separately. For example, two webs may be heat sealed before the third web is added and heat sealed.

The invention is illustrated in the examples which follow.

EXAMPLE 1

Bottom web 11 is a spunlaced polyester-cellulose blended non-woven sheet (Sontara) having a weight of 1.8 ounces per square yard.

Intermediate web 12 is a coextruded film having a first sealant layer 121 of polypropylene (Fina 8473) a tie layer 123 of PIB-modified HDPE (Paxon 3204) and a second sealant layer 122 of a blend of 60% PIB-modified HDPE (Paxon 3204) and 40% polypropylene (Fina 8473).

Top web 13 is a clear plastic laminate four mils in thickness. Top layer 133 is polyester (LBT Mylar) and bottom layer 132 is polypropylene (Exxon Extrel 15 v).

The three webs are placed in registration as shown in FIG. 5 and heat sealed between upper and lower heat seal platens. The bottom platen temperature is 350° F. Dwell time and top platen temperature are varied as shown in Table I. A length of double sided tape carrying a release paper cover strip is applied as shown in FIGS. 6 and 7.

Figure 8:
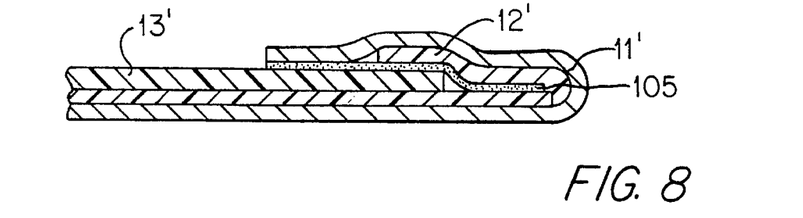
FIG. 8 is an enlarged, diagrammatic cross sectional view similar to FIG. 7, but showing the pouch after folding an end thereof.

The pouch is 18"×34" in size. A 10"×20" tray loaded with medical instruments and weighing 15 pounds is inserted into the cavity 16 of the pouch using a loading device as depicted in FIGS. 9 and 10 by first removing the release paper covering the adhesive tape and then folding the pouch and sealing the adhesive tape to the pouch such that the access opening to the pouch cavity is sealed as shown in FIG. 8. The sealed pouch is then subjected to steam sterilization in an autoclave at 270° F. for 10 minutes. The pouch shows no visual effects after autoclaving, the webs and seals being free of visible distortion, crinkling and the like. Seal strength is as shown in Table I.

TABLE I

| RUN NO. | TOP PLATEN (°F.) | DWELL TIME (SEC.) | SEAL SEAL 14 | STRENGTH SEAL PRE-AUTO | (LBS/IN) 15 POST-AUTO |
|---|---|---|---|---|---|
| 1 | 230 | 1-½ | Permanent* | 2.45 | 1.78 |
| 2 | 245 | 1 | Permanent* | 2.77 | 1.79 |
| 3 | 245 | 1-½ | Permanent* | 2.79 | 1.81 |

*Webs tear before seal.

After storage for 30 days at room temperature and ambient humidity, the sterilized tray is free of contamination.

What is claimed is:

1. A steam-sterilizable pouch comprising:

a steam-permeable non-woven bottom web;

a multilayer intermediate web superposed with and bonded to said bottom web, said intermediate web being substantially steam-impermeable, having a perforated region to permit passage of steam, and having a bottom layer and a top layer bonded thereto;

a steam impermeable top web superposed with and bonded to the top layer of said intermediate web by a first line heat seal, said first line heat seal defining limits of a cavity between said top web and said intermediate web for receiving an object to be sterilized, at least one area of said package being free of said first line heat seal, said seal-free area forming an access opening for inserting an item to be sterilized into said cavity, said access opening being sealable such that, when sealed, the sealed access opening forms with said first line heat seal a continuous steam-impervious seal enclosing said cavity, at least a portion of said first line heat seal being a peelable seal which, after steam sterilization of the pouch at a temperature of 270° F., has a peel strength of from ¾ to 5 pounds per inch and is reliably sealed such that the shelf life of a sealed sterilized package is at least 30 days, said peel seal portion of said first line heat seal extending a distance such that, when peeled open, the contents of the cavity are readily removable from said cavity;

said intermediate web being bonded to said bottom web by a second line heat seal peripherally outside the perforated steam-permeable region of said intermediate web such that, when the pouch is sealed, steam can penetrate into said cavity only after passing through said bottom web and then through the perforated region of the intermediate web.

2. A steam-sterilizable pouch according to claim 1 wherein said intermediate web is a coextrusion.

3. A steam-sterilizable pouch according to claim 1 wherein said top web is a lamination.

4. A steam-sterilizable pouch according to claim 1 wherein said first line heat seal is positioned directly above said second line heat seal.

5. A steam-sterilizable pouch according to claim 1 wherein said pouch is rectilinear, wherein said first and second line heat seals extend in marginal areas on three sides of the package, and wherein said access opening is located on the fourth side of the package.

6. A steam-sterilizable pouch according to claim 1 wherein said pouch further comprises means for sealing said access opening.

7. A steam-sterilizable pouch according to claim 6 wherein said sealing means comprises an adhesive strip.

8. A steam-sterilizable pouch according to claim 5 wherein the top intermediate and bottom webs are positioned with three sides in coincident, wherein the intermediate web is larger than said top web such that its fourth side extends beyond the fourth side of said top web, and wherein the bottom web is larger than the intermediate web such that its fourth side extends beyond the fourth side of said intermediate web.

9. A steam-sterilizable pouch according to claim 8 wherein the fourth side of said intermediate web is sealed to the bottom web whereby the intermediate web is sealed to the bottom web by a continuous seal peripherally outside said perforated area.

10. A steam-sterilizable pouch according to claim 9 wherein said fourth side seal comprises an adhesive seal.

11. A steam-sterilizable pouch according to claim 8 wherein said pouch further comprises means for sealing the access opening between said intermediate and top webs.

12. A steam-sterilizable pouch according to claim 11 wherein said sealing means comprises an adhesive strip extending across the upper surface of the intermediate web in the portion of said intermediate web which extends beyond the fourth side of said top web.

13. A steam-sterilizable pouch according to claim 12 wherein said pouch further comprises a fold line extending across the pouch at a location outside the fourth side of said top web whereby said access opening is sealable by folding the pouch along the fold line to position the adhesive strip on said access opening.

14. A steam-sterilizable pouch according to claim 12 wherein said adhesive comprises a pressure sensitive adhesive.

15. A steam-sterilizable pouch according to claim 12 wherein said adhesive strip further extends across the upper surface of the bottom web in the portion of said bottom web which extends beyond the fourth side of said intermediate web whereby the adhesive strip seals the fourth side of the intermediate web to the bottom web whereby the intermediate web is sealed to the bottom web by a continuous seal peripherally outside said perforated area.

16. A steam-sterilizable pouch according to claim 1 wherein said bottom web comprises a non-woven polyester.

17. A steam-sterilizable pouch according to claim 1 or 16 wherein the bottom layer of said intermediate web comprises polypropylene or a propylene copolymer.

18. A steam-sterilizable pouch according to claim 1 wherein the top web comprises a top layer which comprises a polyester or nylon and a bottom layer which comprises polypropylene or a propylene copolymer.

19. A steam-sterilizable pouch according to claim 1 or 18 wherein the top layer of said intermediate web comprises PIB-modified HDPE or a blend thereof with up to 90% polypropylene or a propylene copolymer.

20. A steam-sterilizable pouch according to claim 1 wherein said bottom web comprises spunlaced polyester, the bottom layer of said intermediate web comprises polypropylene or a propylene copolymer, the top layer of said intermediate web comprises PIB-modified HDPE or a blend thereof with up to 90% polypropylene or propylene copolymer, the bottom layer of said top web comprises polypropylene or propylene copolymer, and the top layer of said top web comprises polyester or nylon.

21. A steam-sterilizable pouch according to claim 20 wherein said intermediate web comprises a tie layer between its top and bottom layers said tie layer comprising PIB-modified HDPE, rubber-modified polypropylene, or a propylene copolymer.

22. A method of steam sterilizing an object which comprises:

(a) providing a pouch which comprises:
  a steam-permeable bottom web;
  a multilayer intermediate web superposed with and bonded to said bottom web, said intermediate web being substantially steam-impermeable, having a perforated region to permit passage of steam, and having a bottom layer and a top layer bonded thereto;
  a steam impermeable top web superposed with and bonded to the top layer of said intermediate web by a first line heat seal, said first line heat seal defining limits of a cavity between said top web and said intermediate web for receiving an object to be sterilized, at least one area of said package being free of said first line heat seal, said seal-free area forming an access opening for inserting an item to be sterilized into said cavity, said access opening being sealable such that, when sealed, the sealed access opening forms with said first line heat seal a continuous steam-impervious seal enclosing said cavity, at least a portion of said first line heat seal being a peelable seal which, after steam sterilization of the pouch at a temperature of 270° F., has a peel strength of from ¾ to 5 pounds per inch and is reliably sealed such that the shelf life of a sealed sterilized package is at least 30 days, said peel seal portion of said first line heat seal extending a distance such that, when peeled open, the contents of the cavity are readily removable from said cavity;
  said intermediate web being bonded to said bottom web by a second line heat seal peripherally outside the perforated steam-permeable region of said intermediate web such that, when the pouch is sealed, steam can penetrate into said cavity only after passing through said bottom web and then through the perforated region of the intermediate web, said second line heat seal being a permanent fiber tearing seal;

(b) placing an object to be sterilized in the cavity of the pouch;

(c) sealing said pouch such that the object to be sterilized is sealed in said cavity and such that steam can penetrate into said cavity only after passing through the bottom web and then through the perforated region of the intermediate web;

(d) and subjecting the sealed pouch to steam sterilization at a temperature of at about 270° F. for a time sufficient to sterilize said object.

23. A method according to claim 22 wherein steam sterilization is carried out for at least 3 minutes.

24. A method according to claim 23 wherein steam sterilization is carried out for from 3–10 minutes.

25. A method according to claim 22 wherein the pouch is rectilinear and where said first and second line heat seals extend in marginal areas on three sides of the package and wherein said access opening is located on the fourth side of the package.

26. A method according to claim 22 wherein said pouch comprises a pressure sensitive adhesive strip and wherein step (c) is carried out by applying said adhesive strip across said access opening.

27. A method according to claim 26 wherein stop (c) is carried out by folding the pouch such that the adhesive strip is applied across said access opening.

28. A method according to claim 22 wherein said bottom web comprises a non-woven polyester.

29. A method according to claim 22 or 28 wherein said the bottom layer of said intermediate web comprises polypropylene or a propylene copolymer.

30. A method according to claim 22 wherein the top web comprises a top layer which comprises a polyester or nylon and a bottom layer which comprises polypropylene or a propylene copolymer.

31. A method according to claim 22 or 30 wherein the top layer of said intermediate web comprises PIB-modified HDPE or a blend thereof with up to 90% polypropylene or a propylene copolymer.

32. A method according to claim 22 wherein said bottom web comprises spun bonded polyester, the bottom layer of said intermediate web comprises polypropylene or a propylene copolymer, the top layer of said intermediate web comprises PIB-modified HDPE or a blend thereof with up to 90% polypropylene or propylene copolymer, the bottom layer of said top web comprises polypropylene or propylene copolymer, and the top layer of said top web comprises polyester or nylon.

33. A method according to claim 22 wherein said intermediate web comprises a tie layer between its top and bottom layers, said tie layer comprising PIB-modified HDPE, rubber-modified polypropylene, or a propylene copolymer.

* * * * *